United States Patent [19]

Strobridge

[11] Patent Number: 5,041,281

[45] Date of Patent: * Aug. 20, 1991

[54] OIL IN WATER EMULSION SUNSCREEN COMPOSITION

[75] Inventor: John R. Strobridge, Comstock Park, Mich.

[73] Assignee: Amway Corporation, Ada, Mich.

[ * ] Notice: The portion of the term of this patent subsequent to Apr. 17, 2007 has been disclaimed.

[21] Appl. No.: 494,736

[22] Filed: Mar. 16, 1990

Related U.S. Application Data

[63] Continuation-in-part of Ser. No. 324,306, Mar. 16, 1989, Pat. No. 4,917,883.

[51] Int. Cl.$^5$ .......................... A61K 7/42; A61K 7/44
[52] U.S. Cl. .......................... 424/59; 424/60
[58] Field of Search ...................... 424/59, 60

[56] References Cited

U.S. PATENT DOCUMENTS

| | | | |
|---|---|---|---|
| 3,966,902 | 6/1976 | Chromecek | 424/59 |
| 4,810,489 | 3/1989 | Murray, II et al. | 424/59 |
| 4,894,222 | 1/1990 | Matravers | 424/59 |
| 4,897,259 | 1/1990 | Murray, I et al. | 514/938 |
| 4,917,883 | 4/1990 | Strobridge | 424/59 |

*Primary Examiner*—Shep K. Rose

[57] ABSTRACT

A waterproof oil in water emulsion sunscreen composition is disclosed. The composition includes a film forming portion comprising between about 0.5 and about 20 weight percent of a copolymer of ethylene and vinyl acetate together with a second polymeric film forming agent which increases the substantivity of the film forming composition. This second polymeric film forming agent is present at between about 0.5 and about 10 weight percent. The sunscreen composition also includes between about 1 and about 30 percent sunscreen agent and between about 0.5 and about 10 percent of an emulsifier. In addition, the sunscreen composition includes between about 45 and about 90 percent water. A method of forming the water in oil sunscreen composition is also disclosed.

27 Claims, No Drawings

OIL IN WATER EMULSION SUNSCREEN COMPOSITION

CROSS REFERENCE TO RELATED APPLICATIONS

The present application is a continuation-in-part of application Ser. No. 324,306, filed on Mar. 16, 1989 by the same inventor.

BACKGROUND OF THE INVENTION

The present invention relates to the field of sunscreen compositions, i.e. compositions which, when applied to the skin, provide protection against the damaging effects of ultraviolet radiation. More particularly, the invention relates to the field of sunscreen compositions which are formed as an oil in water emulsion.

In recent years, the general public has become more and more aware of the damaging effects of ultraviolet radiation from the sun. Consequently, sunscreen compositions have become popular for people who spend time in the sun. Generally, such sunscreen compositions include active sunscreen agents, such as Padimate O, which absorb ultraviolet light in the erythemal region (280–320 nanometers), i.e. the region linked to erythema and skin cancer. Those compositions formulated for greater protection typically also include a sunscreen agent, such as oxybenzone, which absorbs ultraviolet light in a broader range (e.g. 280–340).

A challenge in formulating a sunscreen composition is to produce a composition with good substantivity, i.e. retention on the skin. Certainly, a sunscreen compositions effectiveness is tied directly to its ability to stay in place on the skin of the user for the entire time the user is in the sun. As a result, it is important that the composition be resistant to being rubbed off or washed off in water.

To make a sunscreen resistant to being washed off in water, i.e. waterproof, is particularly important in view of the fact that many consumers use sunscreen compositions in connection with water sports. Also, because sunscreen compositions are often used on hot days and/or in connection with strenuous physical activities, it is important that the compositions be waterproof so that it is not lost due to perspiration.

U.S. Pat. No. 4,663,157 to Brock describes an oil in water emulsion sunscreen composition which is reportedly resistant to rubbing off. The composition includes between about 1 and about 20 percent of a sunscreen agent, between about 0.25 and about 3 percent of a copolymer of ethylene and acrylic acid, between about 2 and about 10 percent emulsifier and between about 70 and about 96 percent water. The ratio of the sunscreen agent to the copolymer is stated to be between about 1:12 and about 15:1. This copolymer in this ratio is stated to improve the substantivity, particularly the resistance to rubbing off, of the composition.

U.S. Pat. No. 4,699,779 to Palinczar describes a sunscreen which is reported waterproof. The composition includes from about 15 to about 95 percent water, from about 1 to about 30 percent of an active sunscreen agent, from about 0.1 to about 6 percent ethylcellulose, from about 0.01 to about 12 percent surface active agent, and from about 0.03 to about 5 percent alkaline dispersion promoting agent.

U.S. Pat. No. 4,731,242 to Palinczar describes a sunscreen composition which is also reported to be waterproof. The disclosed composition includes from 15 to about 90 percent monhydric alcohols, from about 1 to about 30 percent of an active sunscreen agent, from about 0.1 to about 40 percent polyamide polymer, from about 0.1 to about 5 percent acrylic acid crosslinked polymer, and from about 0.1 to about 8 percent alkaline neutralizing agent.

SUMMARY OF THE INVENTION

Briefly stated, the present invention is an oil in water emulsion sunscreen composition. The composition includes between about 0.5 and about 20 weight percent of a copolymer of ethylene and vinyl acetate and a second film forming polymer which increases the substantivity of the composition. This second film forming polymer is present at between about 0.5 and about 10 weight percent. The sunscreen composition also includes between about 0.5 and about 10 percent of an emulsifier and between about 1 and about 30 percent of an oil soluble sunscreen agent. In addition, the sunscreen composition includes between about 45 and about 90 percent water.

In accordance with the method aspect of the present invention, a pre-blend of the water insoluble components is prepared which includes a copolymer of ethylene and vinyl acetate together, a second polymeric film forming agent which increases the substantivity of the film forming composition, a fatty acid component of an emulsifier, and a sunscreen agent. This pre-blend is then combined with water and an alkaline saponifying agent with agitation sufficient to form the oil in water emulsion. The alkaline saponifying agent is used to saponify the fatty acid and thus form the oil in water emulsion. Preferably, the alkaline saponifying agent is added to the water before the pre-blend is added. Alternatively, the alkaline saponifying agent is added after the pre-blend and the water have been combined. According to this method, the final composition comprises between about 0.5 and about 20 weight percent of the copolymer of ethylene and vinyl acetate; between about 0.5 and 10 percent of the second polymeric film forming agent; between about 0.5 and about 10 percent of the emulsifier; between about 1 and about 30 percent of the sunscreen agent; and between about 45 and about 90 percent water.

An advantage of the present invention is that sunscreen compositions made in accordance with the invention have been observed to have remarkably improved substantivity in water. As will be described below in connection with the examples, tests have shown that substantivity is retained after immersion in water for 80 minutes. Accordingly, the preferred compositions of the present invention can be designated as "waterproof" or "water resistant" under the guidelines published in the FDA monograph published in the *Federal Register.* Vol. 43, No. 166, pp. 38206–38269

Another advantage of the present invention is that it provides this level of substantivity in an oil in water emulsion vehicle. In particular, oil in water emulsions are typically more aesthetically pleasing in that they have the appearance and feel of a cream or lotion.

Yet another advantage of the present invention is that the compositions produced have been observed to be quite stable. That is, the emulsions do not separate over time.

It is noted that, unless otherwise indicated, the percentages stated in this specification and the appended claims are intended to refer to percentages by weight of the total sunscreen composition.

The present invention, together with attendant objects and advantages, will be best understood with reference to the detailed description below.

DETAILED DESCRIPTION OF THE PREFERRED EMBODIMENTS

As mentioned above, the sunscreen composition of the present invention is an oil in water emulsion. This means that the composition includes an internal water insoluble phase in the form of small droplets which are uniformly dispersed and held within the external water phase. Preferably, the droplets vary between about 1 and about 10 microns in size. Generally, an emulsifier, i.e. a surfactant such as a soap, is used to maintain the droplets in suspension.

The basic mechanism of an oil in water sunscreen composition is that once the emulsion is applied to the skin, the water evaporates and thus leaves behind the film forming compound with the active sunscreen agent entrapped therein.

The fact that the composition is made as an oil in water emulsion is advantageous. Generally, the external phase of an emulsion will determine the feel of the product. Thus, the oil in water emulsion of the present invention feels like water when applied to the skin. To most consumers, the feel of an oil in water emulsion is preferable to that of an all oil composition or a water in oil emulsion.

Although oil in water emulsions may be preferred for these reasons, certain challenges are met in formulating an oil in water emulsion sunscreen composition, especially one that is intended to be waterproof. In particular, while the oil phase has to be dispersible in the water phase during production of the composition, it is important that the oil phase not be redispersible in water after being applied to the skin. Otherwise, the oil phase is easily removed in water. For example, the emulsifiers used to achieve or maintain the dispersion of the oil phase also typically tend to redisperse the oil phase upon contact with water, leading to a loss of efficacy.

It is currently believed that the increased substantivity in water of the present invention may be due, at least in part, to the inclusion of the copolymer of ethylene and vinyl acetate monomers (EVA copolymer).

As its name suggests, the EVA copolymer is made up of ethylene monomers, i.e. $CH_2=CH_2$, and vinyl acetate monomers, i.e. $CH_3COOCH=CH_2$. The polymeric formula is $CH_3(CH_2)x(CH_2CHOOCHCH_3)y$ The ratio of x:y is from 20:1 to about 4:1, and preferably 7.6:1. The average molecular weight is greater than about 2,000. The hardness (dmn ASTMD-5) of the EVA copolymer is preferably between about 4 and about 80, most preferably about 9.5. The drop point (ASTMD3954) is preferably between about 60 and about 103° C., most preferably about 95° C.

The amount of EVA copolymer used is between about 0.5 and about 20 percent. More preferably, the amount is between about 1 and about 10 percent.

Preferably, the EVA copolymer is added to the composition in particulate form with an average particle size small enough to be readily dispersed in the emulsion.

Most preferably, the EVA copolymer is one such as that obtainable from Allied Signal under the designation "AC-400". Alternatively, EVA copolymer from Allied Signal under the designations "AC-400A, AC-405, AC-405S, AC-405T, AC-405T, AC-430" or from DuPont Chemical under the designation "Elvox 40P" can also be used.

While not wishing to be bound by any particular theory, the importance of the EVA copolymer is believed to be explained by the following. The EVA copolymer not only acts as a film former in conjunction with the second film former, but also acts, to some extent, to lower the Hydrophyllic Lipophyllic Balance (HLB) of the surfactant system. A low HLB indicates that a system has more of a lipophyllic nature than a hydrophyllic nature. Thus, when the EVA copolymer is blended with the oil phase ingredients, it tends to promote an emulsion of those ingredients when blended with the water phase. Beneficially, after the composition is dried down, i.e. after application to the skin, the system does not reform an emulsion upon contact with water.

A second film forming polymer, i.e. in addition to the EVA copolymer, is included in the composition of the present invention so as to increase the substantivity of the entire composition. The second film forming polymer is present at between about 0.5 and about 10 percent, preferably between about 1 and about 5 percent. A particularly preferred second polymer is a copolymer of eicosene and polyvinylpyrrolidone (EPVP copolymer). The polymeric formula for the EPVP copolymer is as follows:

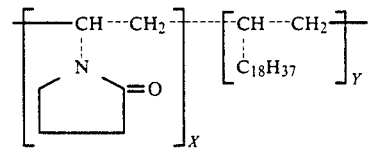

Most preferably, the EPVP copolymer is one such as that sold by GAF under the designation "Ganex V-220". This particular EPVP copolymer has an average molecular weight of about 8600.

Alternatively, other film forming polymers can be used. For example, other copolymers with polyvinyl pyrrolidone, such as those PVP copolymers with other long chain alkanes, i.e. $C_{16}$-$C_{20}$. A suitable Polyvinyl pyrrolidone hexadecane copolymer is sold by GAF under the designation "Ganex V-216". Also, copolymers of octadecane and maleic anhydride can be used, such as that sold by Gulf Science under the designation "PA-18". In addition, combinations of any of the above can also be used.

As with the EVA copolymer, it is preferred to add the second film forming polymer in particulate form wherein the particles are small enough to be easily dispersed.

The composition of the present invention includes between about 1 and about 30 percent of an active sunscreen agent. As used herein, the term active sunscreen agent is intended to refer to a compound which absorbs ultraviolet radiation in the range which is harmful to human skin. Naturally, it is important that the sunscreen agent is non-irritating, non-toxic and compatible with the other ingredients used in the composition.

Suitable active sunscreen agents include the following compounds: Padimate O (octyl p-dimethylaminobenzoate); Padimate A (amyl p-dimethylaminobenzoate); Oxybenzone (2-hydroxy-4-methoxybenzophenone); ethylhexyl p-methoxycinnamate; PABA (para-aminobenzoic acid); Cinoxate (2- ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]-aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); 2-phenylbenzimidazole-5-sulfonic acid); Sulisobenzone (5-benzoyl-4-hydroxy-2-methoxybenzenesulfonic acid); triethanolamine salicylate; 4-tert. butyl-4-methoxydibenzoylmethane; and benzalphthalide. Preferably, a combination of sunscreen agents selected from the group consisting of Padimate O, Oxybenzone, and ethylhexyl p-methoxycinnamate is used.

As mentioned, the present invention may contain from about 1% to about 30% by weight of one or a combination of these active sunscreen agents. The preferred total amount of the active sunscreen agent is dependent upon the particular agents chosen as well as the particular SPF value (sun protection factor) desired to be obtained. The preferred sunscreen agents in the present invention are Padimate O in amounts from 0.5% to about 8% by weight; oxybenzone in amounts from 0.5% to about 6% by weight, and ethylhexyl p-methoxycinnamate in amounts from about 0.5% by weight to about 7% by weight.

The composition of the present invention also includes an emulsifier in an amount between about 0.5 and about 10 percent. Suitable emulsifiers can be any of a wide variety capable of facilitating an oil in water emulsion. U.S. Pat. No. 3,755,560, Aug. 28, 1973 to Dickert et al and U.S. Pat. No. 4,421,769, Dec. 20, 1983 to Dixon et al., both incorporated by reference herein, disclose several such emulsifiers. Anionic or nonionic emulsifiers are preferred. McCutcheon's *Detergents and Emulsifiers*, North American Edition, 1983, incorporated herein by reference, also discloses a number of suitable emulsifiers.

Suitable emulsifier types include soaps, fatty acid amides, ethoxylated fatty acids, ethoxylated esters, ethoxylated ethers, ethoxylated alcohols, phosphated esters, polyoxyethylene fatty ether phosphates, acyl lactylates, and mixtures thereof.

Preferably, the emulsifiers used in the present invention are soaps which are formed in situ by blending long chain fatty acids with the water insoluble portion, adding the water containing an alkaline compound which will saponify the long chain fatty acids.

Alternatively, the water is added without the alkaline, and after the water insoluble portion is well dispersed in the water, the alkaline saponifying agent is added to saponify the long chain fatty acids.

Preferably, the long chain fatty acids are selected from the group consisting of stearic, isostearic, palimitic, oleic, and linoleic acid, as well as combinations thereof. Most preferably, the long chain fatty acid is isostearic acid.

When the emulsifier is a soap formed by in situ saponification, the alkaline agent is preferably selected from the group consisting of ammonium hydroxide, sodium hydroxide, potassium hydroxide, and tertiary amines, as well as combinations thereof. Most preferably, ammonium hydroxide is used.

The emulsifier, or mixture of emulsifiers, is present at a level of from about 0.5% to about 10%, preferably about 5%.

The sunscreen composition of the present invention includes between about 45 and about 90 percent water. Distilled or deionized water is preferred If hard water is used, a chelating agent, such as tetrasodium EDTA, should also be used at levels between about 0.05 and about 0.15 percent.

Preferably, the present composition also contains between about 0.05 and about 5.0 percent of a thickener. Suitable thickeners are those ingredients which produce an increase in the viscosity of the composition. Naturally, the thickeners should be non-toxic, non-irritating, and compatible with the other ingredients in the composition. Preferably, the thickeners are selected from the group consisting of synthetic polymers, modified cellulose compounds, nonionic gums, and clays. Examples of synthetic polymers include carboxyvinyl polymers and acrylic acid crosslinked polymers. Examples of modified cellulose compounds include hydroxyethylcellulose and hydroxypropylcellulose. Examples of nonionic gums include xanthan gum, gum arabic, and guar gum. Clays can be selected from those clays which are swellable in water to provide a thickening effect. Examples include fumed silica, amorphous silica, sodium magnesium silicate and colloidal magnesium aluminum silicate.

The preferred composition of the present invention also include from about 1 to about 30 percent of water insoluble emollients, i.e. compounds which are known to act as skin softeners. The water insoluble emollient can also be used to control the viscosity which in turn affects the amount of product deposited on the skin and the texture and cohesiveness of the polymer film. Preferably, the water insoluble emollients are selected from the group consisting of lanolin, isopropyl myristate, glyceryl stearate, cetyl alcohol, and dimethicone, together with combinations thereof.

It is also preferred that the composition include between about 0.5 and about 25 percent of suspended particulate matter. Preferably, this suspended particulate matter will be an opacifyer, such as titanium dioxide, which not only adds a white pigment to the composition, but also acts as a sunscreen agent in and of itself. In addition to titanium dioxide, other compounds that can be used for this purpose include zinc oxide, talc, kaolin, calcium carbonate, and magnesium oxide, as well as combinations thereof.

The preferred composition may also include a fragrance in order to impart an appropriate pleasing odor to the composition.

The preferred composition may further include an appropriate amount of a preservative selected so as to provide protection against spoilage. The most preferred preservative is polymethoxybicyclic oxazolidine which is available from Huls under the designation "Nuosept C". The preferred level of this preservative is 0.5% by weight.

Alternatively, the preservative can be a combination of the following: 0.05 percent methylchloroisothizolinone (and) methylisothiazolinone (available from Rhom and Haas under the designation "Kathon CG"; 0.25 percent methyl parabin; and 0.05 propyl parabin. Another suitable preservative system includes the following: 0.20 quaternium 15 (available from Dow Chemical under the designation "Dowicill 200"; 0.5 percent benzyl alcohol; 0.25 methyl parabin; 0.05 propyl parabin; and 0.1 tetrasodium EDTA. The weight percentages given are based on the weight of the commercially available formulations of the above preservative ingredients.

In general, the preferred method of forming the oil in water emulsion sunscreen composition of the present invention begins by making a pre-blend of the oil phase ingredients of the composition, i.e. the film forming polymers, the sunscreen agent, and the fatty acid component of the emulsifier. This pre-blend is then added to water, which water includes the alkaline saponifying agent. The mix is agitated sufficiently to form the oil in water emulsion.

Alternatively, the pre-blend is added to the water phase with agitation. Once the oil phase is well-dispersed, the alkaline saponifying agent is then added to form the soap and thereby facilitate the formation of the oil in water emulsion.

The most preferred method of putting the above-described components together to make the oil in water emulsion of the present invention is as follows. A pre-blend of the oil phase is made. In particular, the EVA copolymer, the EPVP copolymer, the sunscreen agent, the fatty acid component of the emulsifier, the emollients, if any, are added together and blended to form a homogeneous dispersion, i.e. no lumps. Most preferably, these components are mixed in a "sweep wall" type agitator at a temperature between about 70° and 110° C.

The water phase including the water and any thickeners are also premixed to form a homogeneous blend. Most preferably, the water phase is mixed in a turbine type mix tank at between about 70° and 95° C.

The oil phase is added into the water phase with continuous vigorous agitation. The temperature of the mix is dropped to 65° C. At this point, the alkaline saponifying agent is added to the mix while maintaining the temperature and agitation. As its name suggests, the agent saponifies the fatty acid to produce the soap and thereby emulsify the composition. A visual indication that the fatty acid has been neutralized is that the mix takes on a whiter, smoother appearance.

After this point, the mixture is forced cooled under continuous agitation down to 50° C., at which point, the preservative and fragrance are added. The mixture is force cooled to 45° C whereupon it can be immediately packaged or stored for later packaging.

EXAMPLES

Example 1 through 5 were made with the following composition. Example 1 is illustrative of the most preferred embodiment of the present invention with the exception that the pre-blend was added to water and agitated, after which the alkaline saponifying agent was added with continued agitation. Examples 2 and 3 are comparative examples. Example 2 was made without the EVA copolymer. Example 3 was made without a second film forming polymer, such as EPVP.

| Ingredient | Ex. 1 | Ex. 2 | Ex. 3 | Ex. 4 | Ex. 5 |
|---|---|---|---|---|---|
| Water | 58.85 | 64.85 | 61.85 | 56.20 | 64.35 |
| Padimate O | 8.00 | 8.00 | 8.00 | 8.00 | 6.00 |
| Ethylhexyl p-methoxycinnamate | 4.00 | 4.00 | 4.00 | 7.00 | — |
| Oxybenzone | 4.00 | 4.00 | 4.00 | 6.00 | 2.00 |
| Ethylene Vinyl Acetate Copolymer | 6.00 | — | 6.00 | 6.00 | 6.00 |
| Eicosene PVP Copolymer | 3.00 | 3.00 | — | 3.00 | 3.00 |
| Isostearic Acid | 5.00 | 5.00 | 5.00 | 5.00 | 5.00 |
| Ammonium Hydroxide | 0.40 | 0.40 | 0.40 | 0.40 | 0.40 |
| Glyceryl Stearate | 2.25 | 2.25 | 2.25 | 1.50 | 2.25 |
| Cetyl Alcohol | 4.00 | 4.00 | 4.00 | 3.50 | 4.50 |
| Isopropyl Myristate | 3.00 | 3.00 | 3.00 | — | 5.00 |
| Lanolin | 0.10 | 0.10 | 0.10 | 0.10 | 0.10 |
| Allantoin | 0.05 | 0.05 | 0.05 | 0.05 | 0.05 |
| Carbomer 941 | 0.15 | 0.15 | 0.15 | 0.15 | 0.15 |
| Xanthan Gum | 0.20 | 0.20 | 0.20 | 0.10 | 0.20 |
| Fragrance | 0.50 | 0.50 | 0.50 | 0.50 | 0.50 |
| Preservative | 0.50 | 0.50 | 0.50 | 0.50 | 0.50 |
| Titanium Dioxide | — | — | — | 2.00 | — |

These ingredients were put together as described above described above. In particular, the Padimate 0, Ethylhexyl p-methoxycinnamate, oxybenzone, EVA copolymer, EPVP copolymer, isostearic acid, glyceryl stearate, lanoline, and isopropyl myristate were combined in a pre-blend. The water, Carbomer 941, xanthan gum, and allontoin were combined separately. These two phases were added with vigorous agitation. The ammonium hydroxide was added to saponify the isostearic acid. The fragrance and preservative were added at the last step. In Example 4, the titanium dioxide was added with the water phase, although the suspended particulate can also be added with the oil phase.

It was observed that Example 1 resulted in an aesthetically pleasing, opaque, white, creamy looking composition. In the in vitro tests described below, the substantivity of the composition, particularly in water, was found to be excellent.

Example 2 was performed the same as Example 1 except that it contained no ethylene vinyl acetate. This composition had a higher viscosity. The composition also showed low substantivity in the in vitro test.

Example 3 was performed the same as Example 1 with the exception that the EPVP copolymer was eliminated. The resultant composition was white and showed poor substantivity in the in vitro test.

Example 4 was performed the same as Example 1 with the exceptions that more sunscreen agents, including titanium dioxide, were added. Also, isopropyl myristate added and the levels of glyceryl stearate and cetyl alcohol were modified to improve viscosity. This composition had an appearance similar to that of Example 1. The in vitro substantivity results were excellent. The in vivo tests described below showed that this particular composition had an SPF of 30+.

Example 5 was performed the same as Example 1 except that the levels of sunscreen agent were adjusted to produce an SPF of 8. Also, the levels of isopropyl myristate, glyceryl stearate, and cetyl alcohol were adjusted to achieve a viscosity similar to that in Example 1. This composition had excellent substantivity as measured in the in vitro tests.

Example 6 was performed the same as Example 4 except that the alkaline saponifying agent was added to the water prior to adding the pre-blend of water insoluble ingredients. It was found that adding the alkaline saponifying agent to the water before adding the pre-blend did not adversely affect the properties of the oil in water emulsion produced. This was an important observation because it allows for greater flexibility in the equipment required and the size of the batches produced. Example 6 was tested in vivo and found to possess the same efficacy and substantivity as Examples 1-5 above.

The sunscreen compositions made in the examples above were tested in vitro to compare their substantivity to a surface upon exposure to water. The test was designed to be simple and reproducible and yet provide an evaluation of the substantivity of the compositions in a worst case situation.

The test began by spreading a thin layer, i e. 0.002 ml/cm$^2$, of the composition on a glass slide. The composition was allowed to dry down for 20 minutes at ambient temperatures. The glass slide was then placed in a 250 ml. beaker containing soft water, i.e. 5 grains. Earlier tests had shown that substantivity was harder to achieve in distilled water than in either soft water, hard water (12+grains) or sea water. Soft water was thus chosen to best reflect the real world. The water in the beaker was stirred by magnetic stirring bar at a medium speed. At various times, the water and slide were viewed to determine if the composition had come off of the slide. In particular, if the water turned milky with solubilized/dispersed composition, or if flakes or other pieces of the composition were floating in the water, then that composition was given a poor substantivity rating.

Examples 1, 4, and 5 all showed good substantivity in this test for at least 80 minutes in the stirred water. In particular, the composition stayed in place on the glass slide. The compositions made in Examples 2 and 3 did not show positive results, i.e. the composition was lost to the water. Further tests confirmed that, if a composition had remained in place on the glass slide in stirred water for 80 minutes, the composition would likewise remain in place for several hours under the same condition.

In addition to the aforementioned in vitro test, studies were also conducted to evaluate the performance of sunscreen compositions made according to the preferred embodiments as applied to human skin which was subjected to UV radiation, with and without being immersed in water. In particular, the study was conducted by an independent laboratory in conformance with the monograph published in the *Federal Register.* Vol 43, No. 166, pp. 38206-38269. Basically, the test monitored the Sun Protection Factor (SPF) of each of the compositions before and after immersion in water.

This in vivo testing confirmed that the substantivity shown in the in vitro test described above was indeed representative of the substantivity obtained in the real world. It was somewhat surprising to find that the compositions made according to the preferred embodiments of the invention showed little or no reduction in the SPF value upon immersion in water for 80 minutes or more. This is in contrast with many sunscreen compositions which generally lose effectiveness after immersion in water.

It should be noted that although much of the discussion has involved the use of a copolymer of eicosene and vinyl pyrrolidone, other film forming polymers which increase the substantivity of the composition may also be used. Certainly, these and all other modifications which are within the ordinary skill in the art to make are considered to lie within the scope of the invention as defined by the appended claims.

I claim:

1. An oil in water emulsion sunscreen composition comprising:
   between about 0.5 and about 20 percent of a copolymer of ethylene and vinyl acetate;
   between about 0.5 and about 10 percent of a second film forming polymer which increases the substantivity of the composition;
   between about 0.5 and about 10 percent of an emulsifier;
   between about 1 and about 30 percent of sunscreen agent; and
   between about 45 and about 90 percent water.

2. The sunscreen composition of claim 1 wherein the copolymer of ethylene and vinyl acetate is present in an amount between about 1 and about 10 percent.

3. The sunscreen composition of claim 1 wherein the second film forming polymer is a copolymer with vinyl pyrrolidone.

4. The sunscreen composition of claim 1 wherein the second film forming polymer is a copolymer of vinyl pyrrolidone and a $C_{16}$-$C_{20}$ alkane.

5. The sunscreen composition of claim 1 wherein the second film forming polymer is selected from the group consisting of a copolymer of eicosene and vinyl pyrrolidone, a copolymer of hexadecane and vinyl pyrrolidone, a copolymer of octadecane and maleic anhydride, and combinations thereof.

6. The sunscreen composition of claim 1 wherein the second water insoluble polymeric film forming agent is a copolymer of eicosene and vinyl pyrrolidone.

7. The sunscreen composition of claim 6 wherein the copolymer of eicosene and vinyl pyrrolidone is present in an amount between 1 and 5 percent.

8. The sunscreen composition of claim 1 wherein the emulsifier comprises a fatty acid together with a suitable amount of an alkaline saponifying agent.

9. The sunscreen composition of claim 8 wherein the fatty acid is selected from the group consisting of stearic acid, isostearic acid, palmitic acid, oleic acid, linoleic acid, and combinations thereof.

10. The sunscreen composition of claim 8 wherein the alkaline saponifying agent is selected from the group consisting of ammonium hydroxide, sodium hydroxide, potassium hydroxide, tertiary amine, and combinations thereof.

11. The sunscreen composition of claim 1 wherein the sunscreen agent is selected from the group consisting of Padimate O, Padimate A, Oxybenzone, triethanolamine salicylate, ethylhexyl p-methoxycinnamate, titanium dioxide, and combinations thereof.

12. The sunscreen composition of claim 1 further comprising from about 1 to about 30 percent of a water insoluble emollient selected from the group consisting of lanolin, isopropyl myristate, glyceryl stearate, cetyl alcohol, dimethicone, and combinations thereof.

13. The sunscreen composition of claim 1 further comprising between about 0.5 and about 2.5 of suspended particulate matter selected from the group consisting of titanium dioxide, zinc oxide, talc, kaolin, calcium carbonate, magnesium oxide, and combinations thereof.

14. The sunscreen composition of claim 1 further comprising between about 0.05 and about 5.0 thickener selected from the group consisting of nonionic gums, clays, carboxyvinyl polymers, modified cellulose compounds, and combinations thereof.

15. An oil in water emulsion sunscreen composition comprising:
   between about 1 and about 10 percent of a copolymer of ethylene and vinyl acetate;
   between about 1 and about 5 percent of a copolymer of eicosene and vinyl pyrrolidone;

between about 1 and about 10 percent of a fatty acid together with a sufficient amount of an alkaline saponifying agent added to form an emulsifier;

between about 1 and about 30 percent of sunscreen agent;

between about 0.5 and about 2.5 percent suspended particulate matter;

between about 0.05 and about 5.0 percent thickener;

between about 1 and about 30 percent water insoluble emollient; and

16. A method of producing an oil in water emulsion sunscreen composition comprising the steps of:

mixing a pre-blend including
  between about 0.5 and about 20 percent of a co-polymer of ethylene and vinyl acetate,
  between about 0.5 and 10 percent of a second polymeric film forming agent which increases the substantivity of the film forming composition,
  between about 0.5 and about 10 percent of a fatty acid component of an emulsifier,
  between about 1 and about 30 percent of sunscreen agent;

providing water;

providing an alkaline saponifying agent; and combining said pre-blend, said water, and said alkaline saponifying agent with agitation sufficient to form an oil in water emulsion.

17. The method of claim 16 wherein between about 0.05 and about 5 percent thickener is added to the water before the pre-blend is added.

18. The method of claim 17 wherein the thickener is selected from the group consisting of nonionic gums, clays, carboxyvinyl polymers, modified cellulose compounds, and combinations thereof.

19. The method of claim 16 wherein between about 1 and about 30 percent water insoluble emollient is added to the pre-blend before the pre-blend is added to the water.

20. The method of claim 19 wherein the water insoluble emollient is selected from the group consisting of lanolin, isopropyl myristate, glyceryl stearate, cetyl alcohol, dimethicone, and combinations thereof.

21. The method of claim 16 wherein the alkaline saponifying agent is combined with the water before the pre-blend is added.

22. The method of claim 21 wherein between about 0.05 and about 5 percent thickener is added to the water before the pre-blend is added.

23. The method of claim 21 wherein the thickener is selected from the group consisting of nonionic gums, clays, carboxyvinyl polymers, modified cellulose compounds, and combinations thereof.

24. The method of claim 21 wherein between about 1 and about 30 percent water insoluble emollient is added to the pre-blend before the pre-blend is added to the water.

25. The method of claim 21 wherein the water insoluble emollient is selected from the group consisting of lanolin, isopropyl myristate, glyceryl stearate, cetyl alcohol, dimethicone, and combinations thereof.

26. An oil in water emulsion sunscreen composition comprising:

between about 0.5 and about 20 percent of a copolymer of ethylene and vinyl acetate;

between about 0.5 and about 10 percent of a copolymer with vinyl pyrrolidone which increases the substantivity of the composition;

between about 0.5 and about 10 percent of an emulsifier;

between about 1 and about 30 percent of sunscreen agent; and between about 45 and about 90 percent water.

27. A method of producing an oil in water emulsion sunscreen composition comprising the steps of:

mixing a pre-blend including
  between about 0.5 and about 20 percent of a co-polymer of ethylene and vinyl acetate,
  between about 0.5 and about 10 percent of a co-polymer with vinyl pyrrolidone which increases the substantivity of the composition,
  between about 0.5 and about 10 percent of a fatty acid component of an emulsifier,
  between about 1 and about 30 percent of sunscreen agent;

providing water;

providing an alkaline saponifying agent; and combining said pre-blend, said water, and said alkaline saponifying agent with agitation sufficient to form an oil in water emulsion.

* * * * *

UNITED STATES PATENT AND TRADEMARK OFFICE
CERTIFICATE OF CORRECTION

PATENT NO. : 5,041,281

DATED : August 20, 1991

INVENTOR(S) : John R. Strobridge

Page 1 of 3

It is certified that error appears in the above-identified patent and that said Letters Patent is hereby corrected as shown below:

In column 3, line 50, please delete
"$CH_3(CH_2)x(CH_2CHOOCHCH_3)y$"
and substitute therefor
--$CH_3(CH_2)_x(CH_2CHOOCHCH_3)_y$.--.

In column 3, line 68, please delete the first occurrence of "AC-405T" and substitute therefor --AC-405M--.

In column 5, line 47, please delete "in situ" and substitute therefor --*in situ*--.

In column 5, line 60, please delete "in situ" and substitute therefor --*in situ*--.

In column 8, line 30, please delete "in vitro" and substitute therefor --*in vitro*--.

In column 8, line 36, please delete "in vitro" and substitute therefor --*in vitro*--.

In column 8, line 40, please delete "in vitro" and substitute therefor --*in vitro*--.

In column 8, line 47, please delete "in vitro" and substitute therefor --*in vitro*--.

UNITED STATES PATENT AND TRADEMARK OFFICE
CERTIFICATE OF CORRECTION

PATENT NO. : 5,041,281
DATED : August 20, 1991
INVENTOR(S) : John R. Strobridge It is certified that error appears in the above-identified patent and that said Letters Patent is hereby corrected as shown below:

In column 8, line 48, please delete "in vivo" and substitute therefor --_in vivo_--.

In column 8, line 56, please delete "in vitro" and substitute therefor --_in vitro_--.

In column 9, line 2, please delete "in vitro" and substitute therefor --_in vitro_--.

In column 9, line 35, please delete "in vitro" and substitute therefor --_in vitro_--.

In column 9, line 46, please delete "in vivo" and substitute therefor --_in vivo_--.

In column 9, line 47, please delete "in vitro" and substitute therefor --_in vitro_--.

UNITED STATES PATENT AND TRADEMARK OFFICE
CERTIFICATE OF CORRECTION

PATENT NO. : 5,041,281

DATED : August 20, 1991

INVENTOR(S) : John R. Strobridge

It is certified that error appears in the above-identified patent and that said Letters Patent is hereby corrected as shown below:

COLUMN 11

In claim 15, between lines 16 and 17, please insert a new subparagraph --between about 45 and about 90 percent water.--.

Signed and Sealed this

Seventeenth Day of May, 1994

Attest:

BRUCE LEHMAN

Attesting Officer

Commissioner of Patents and Trademarks